(12) United States Patent
Yoneda

(10) Patent No.: US 6,819,418 B2
(45) Date of Patent: Nov. 16, 2004

(54) ILLUMINATING APPARATUS FOR TESTING

(75) Inventor: Kenji Yoneda, Kyoto (JP)

(73) Assignee: CCS, Inc., Kyoto (JP)

( * ) Notice: Subject to any disclaimer, the term of this patent is extended or adjusted under 35 U.S.C. 154(b) by 0 days.

(21) Appl. No.: 10/280,656

(22) Filed: Oct. 25, 2002

(65) Prior Publication Data
US 2003/0081202 A1 May 1, 2003

(30) Foreign Application Priority Data
Oct. 26, 2001 (JP) ....................... 2001-328441

(51) Int. Cl.$^7$ ............................... G01N 21/00
(52) U.S. Cl. .................................. 356/237.6
(58) Field of Search ............................ 356/237.1–237.6

(56) References Cited

U.S. PATENT DOCUMENTS 4,560,273 A * 12/1985 Ando et al. ............... 356/237.6
5,463,462 A * 10/1995 Ohnishi et al. ............. 356/521

FOREIGN PATENT DOCUMENTS

JP 58743 3/1994
JP 2002-39956 2/2002

* cited by examiner

Primary Examiner—Michael P. Stafira
(74) Attorney, Agent, or Firm—Kirschstein, et al.

(57) ABSTRACT

A cost effective and small illuminating apparatus for testing includes an illuminant having a predetermined illumination angle, a first lens for converging light from the illuminant and converting the light into collimated light, and a second lens for converging light which has passed through throughholes formed in a tested target after having been emitted from the first lens as the collimated light and for making an imager take in the light.

3 Claims, 4 Drawing Sheets

ILLUMINATING APPARATUS FOR TESTING

BACKGROUND OF THE INVENTION

1. Field of the Invention

The present invention relates to an illuminating apparatus for testing which is particularly suitable to examine hole-clogging in a catalyst for automobiles perforated to make through-holes and which is also used to examine conditions of the holes in the substrate perforated to make through-holes or the inner surface of a cylindrical member having through-holes.

2. Description of the Background Art

As the above-mentioned illuminating apparatus for testing, a apparatus for checking whether holes formed in the catalyst for automobiles are clogged or not will be taken up as an example. The apparatus comprises an illuminating means for emitting light on the catalyst from the direction its holes are formed; and a telecentric lens for narrowing the light which has passed through the holes after having been emitted by the illuminating means so that the light can be taken into an imaging means. The light taken into the imaging means is shown on a monitor or the like to determine the presence or absence of clogged holes.

Using the telecentric lens to measure a cubic tested target has the advantage of performing high precision image processing without causing the target to be out of focus; however, it has the disadvantage of increasing the cost of the entire apparatus because of the high price of the lens. The disadvantage becomes pronounced when a tested target to be imaged is large because it requires a large telecentric lens.

SUMMARY OF THE INVENTION

In general, a telecentric lens, which is thicker than other lenses, has the disadvantage that a larger illuminating apparatus is required in the direction of illumination.

In view of the above-described situation, the present invention has the object of providing an illuminating apparatus for testing which is cost effective and small in size.

In order to solve the above-described problems, the illuminating apparatus for testing of the present invention comprises: an illuminating means having a predetermined illumination angle; a first lens for converging light from the illuminating means and converting the light into collimated light; and a second lens for converging light which has passed through through-holes formed in a tested target after having been emitted from the first lens as the collimated light and for making an imaging means take in the light.

The light emitted with a predetermined illumination angle from the illuminating means is converted into collimated light by the first lens, and applied to the tested target. The light passed through the through-holes of the tested target is converged by the second lens to be taken into the imaging means. The light taken into the imaging means is subjected to an imaging process and shown on a monitor or the like, which can determine the presence or absence of clogging in the through-holes. It goes without saying that this apparatus can reduce cost, as compared with apparatus utilizing an illuminating means for emitting collimated light (a surface illuminant which illuminates in the form of surface (also called backlight)). In addition, utilizing the illuminating means for emitting light with an illumination angle can miniaturize the illuminating means itself. Since the tested target to be imaged does not change its position, it is meaningless to use the conventional telecentric lens, and it does not cause any problem to use a normal lens.

The illuminating apparatus for testing can comprise: an illuminating means having a predetermined illumination angle; a first total reflection mirror for changing the orientation of the optical axis of light emitted from the illuminating means to a nearly orthogonal direction; a second total reflection mirror for changing the orientation of the optical axis of light reflected by the first total reflection mirror to a nearly orthogonal direction, thereby turning the reflected light to the direction opposite to the direction the illuminating means emits light; a first lens for converging the light reflected by the second total reflection mirror and converting the light into collimated light; a second lens for converging light which has passed through through-holes formed in a tested target after having been emitted from the first lens as the collimated light; a third total reflection mirror for changing the orientation of the optical axis of light from the second lens to a nearly orthogonal direction; and a fourth total reflection mirror for changing the orientation of the optical axis of the light reflected by the third total reflection mirror to a nearly orthogonal direction, thereby making an imaging means take in the reflected light towards the same direction as the direction the illuminating means emits light.

The orientation of the light from the illuminating means is changed to the direction opposite to the direction of illumination by the first total reflection mirror and the second total reflection mirror. Utilizing the two total reflection mirrors expands the illumination angle of the light emitted from the illuminating means at two steps. The light reflected by the second total reflection mirror is converted into collimated light by the first lens and applied to the tested target. The light passed through the through-holes of the tested target is converged by the second lens, and its orientation is changed to the same direction as the direction the illuminating means emits light via the third total reflection mirror and the fourth total reflection mirror. Then the light is taken in by the imaging means. Using the two total reflection mirrors can secure the light converged by the second lens to be converged in two steps so as to be taken in the imaging means. In addition, arranging the illuminating means and the imaging means by being displaced from the direction to radiate the tested target can achieve the miniaturizing of the illuminating apparatus in the direction of illumination, as compared with the case where they are aligned in the direction of illumination.

Adopting Fresnel lenses as the first lens and the second lens can achieve further downsizing of the illuminating apparatus. Fresnel lenses, which are readily processed, could be made into a square contour or drilled.

When the tested target has a lot of fine holes such as a catalyst for automobiles, the illuminating apparatus for testing is useful.

The illuminating apparatus can be miniaturized in the direction orthogonal to the direction to emit light by arranging the illuminating means and the imaging means on the same side so that the optical axis of the illuminating means and the imaging center axis of the imaging means are substantially in a coaxial position.

Forming the second lens to be a workbench of the tested target not only makes a special workbench unnecessary but also puts the tested target as close to the imaging means as possible.

DESCRIPTION OF THE PREFERRED EMBODIMENTS

Figure 1:
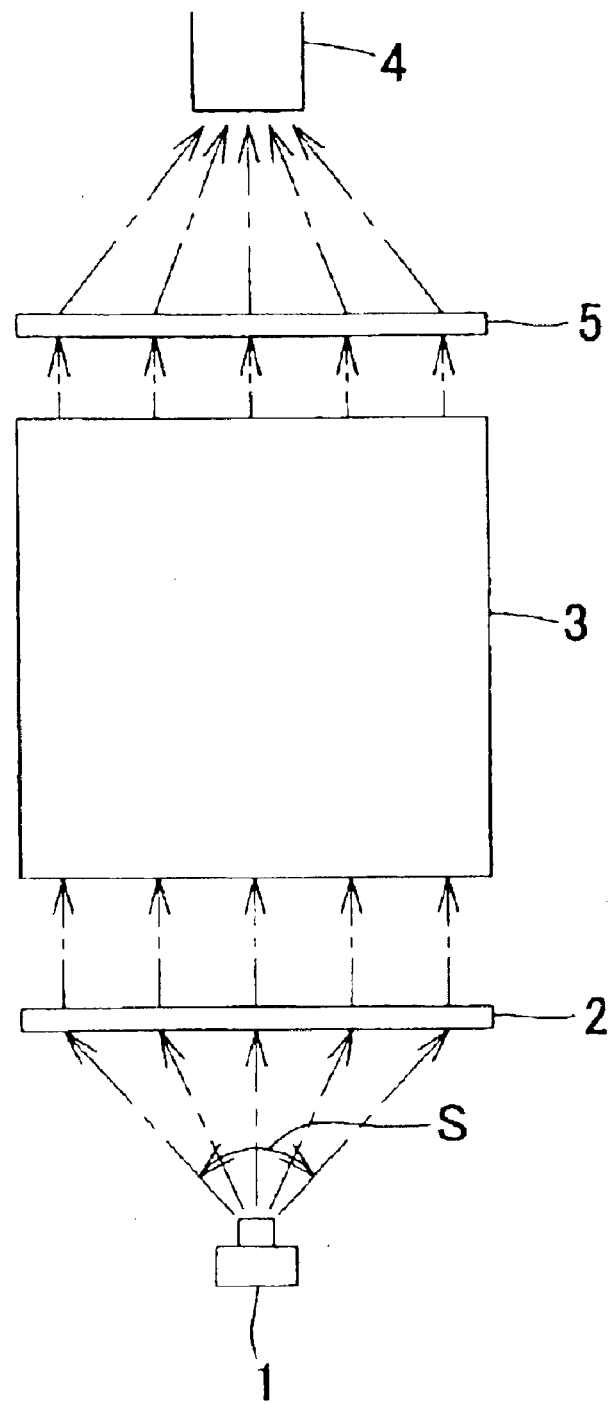
FIG. 1 is a diagrammatic sketch of the first illuminating apparatus for testing.
Figure 4:
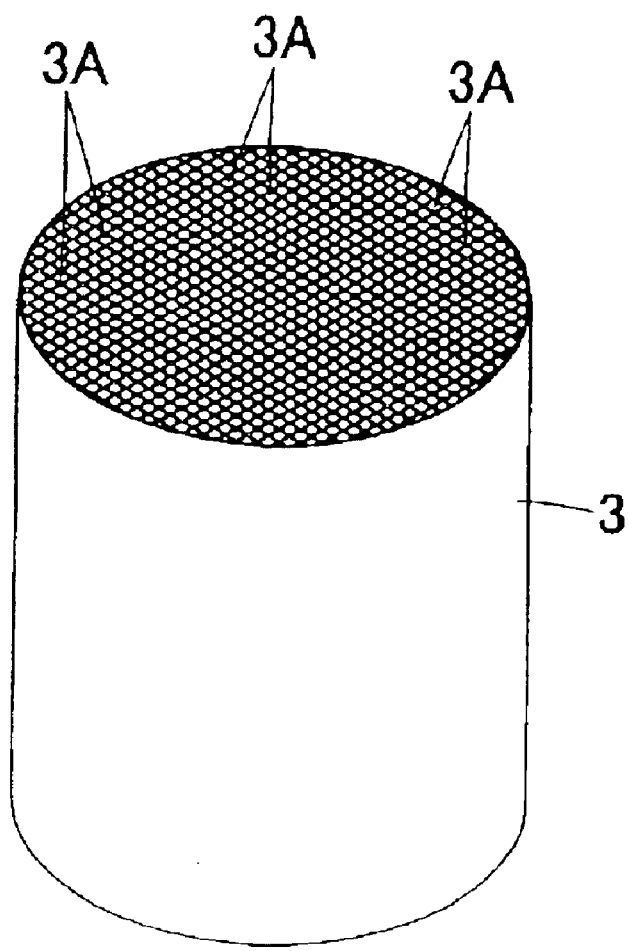
FIG. 4 is a perspective view of the catalyst for automobiles.

FIG. 1 shows the illuminating apparatus for testing of the present invention. The illuminating apparatus for testing includes an illuminating means 1 having a predetermined illumination angle S; a first Fresnel lens 2 as a first lens for converging the light from the illuminating means 1 and converting it into collimated light; and a second Fresnel lens 5 as a second lens for converging the light which has passed through through-holes 3A (refer to FIG. 4) formed in a catalyst 3 of the automobile as the tested target after having been emitted from the first Fresnel lens 2 as the collimated light, and for making the imaging means 4 such as a CCD camera take in the light. The illuminating means 1, the first Fresnel lens 2, and the second Fresnel lens 3 are arranged in the direction the illuminating means emits light. The illuminating apparatus for testing is mainly used to check the presence or absence of clogging in the holes formed in the catalyst (ceramics or the like) 3 for automobiles, and can also be used to examine conditions of the holes in the substrate perforated to make through-holes or the inner surface of a cylindrical member having through-holes. Instead of using the imaging means 4 to show images on a monitor or the like by image processing, light emitted from the second Fresnel lens 5 could be visually checked while omitting the imaging means 4 so as to determine whether the holes in the catalyst 3 are clogged or not. In FIG. 1, all components are illustrated in an unfixed state; however, actually, all components are housed in a casing. Although the location of the catalyst 3 disposed between the two Fresnel lenses 2 and 5 is preferably closer to the second Fresnel lens 5, that is, closer to the imaging means 4, it could be closer to the first Fresnel lens 2.

As shown in FIG. 1, the light emitted from the illuminating means 1 is converted into collimated light by the first Fresnel lens 2 and then applied on the catalyst 3. The light passed through the holes 3A in the catalyst 3 is converged by the second Fresnel lens 5 and taken into the imaging means 4. The illumination angle S of the illuminating means 1 is not restricted to the one shown in the drawing, but can be modified depending on the size of the tested target or other conditions. It is also possible to design the illuminating means 1 in such a manner that the illumination angle S is variable.

The Fresnel lenses 2 and 5 can be shaped to have circular or rectangular appearance by cutting circular belt-shaped grooves. Besides this shape, they can be of any other shape. Using Fresnel lenses are advantageous to miniaturize the illuminating apparatus for testing, but other lenses can be used instead.

Figure 2:
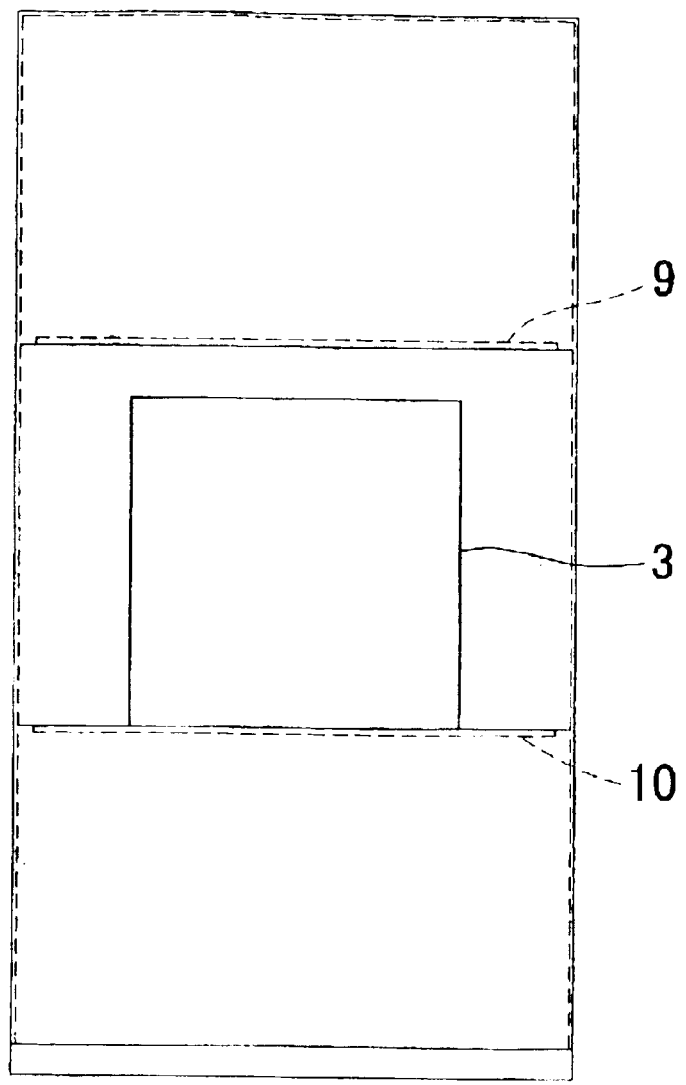
FIG. 2 is the front view of the second illuminating apparatus for testing.
Figure 3:
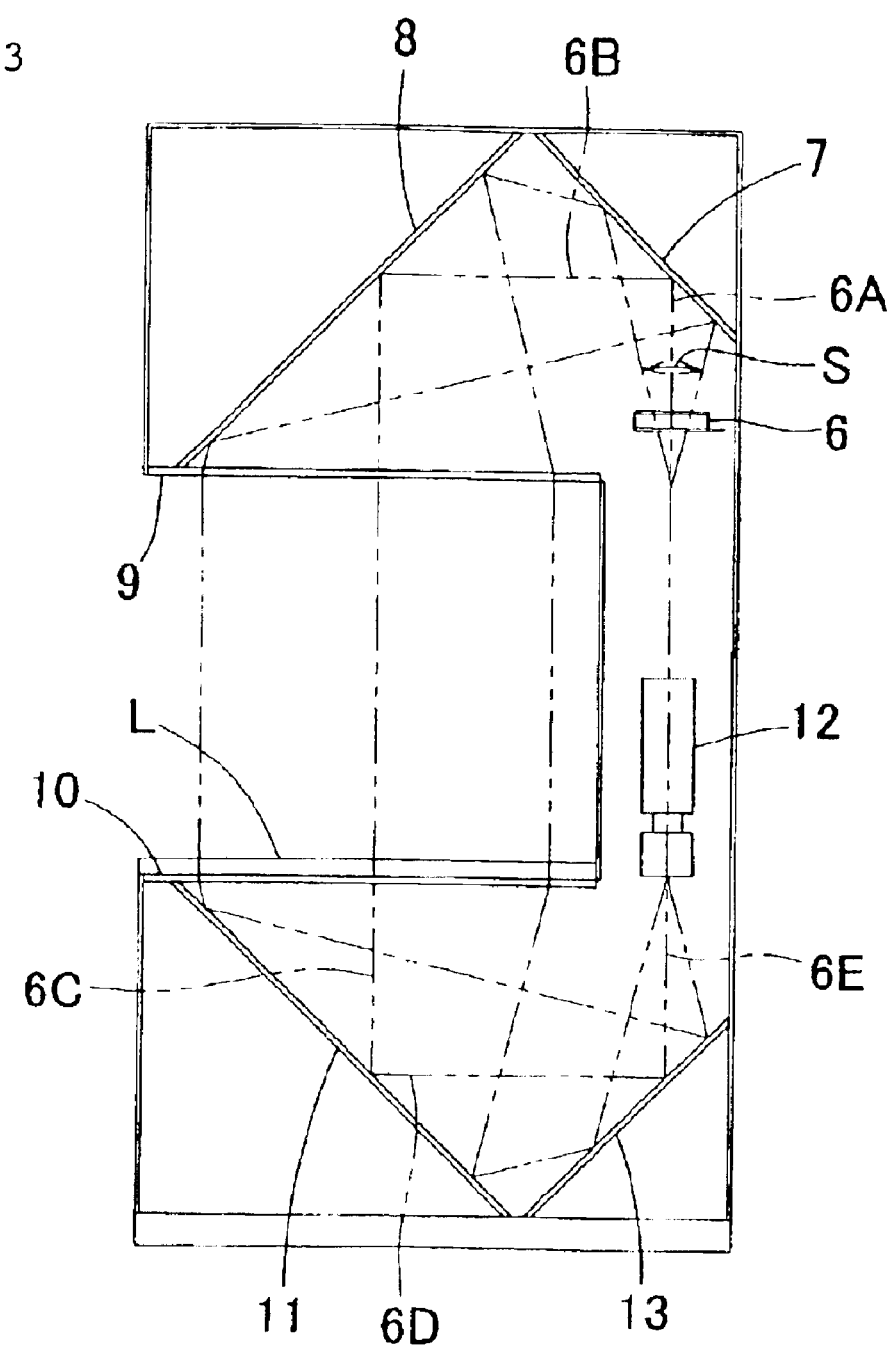
FIG. 3 is a vertical cross sectional view of the second illuminating apparatus for testing.

The above-described illuminating apparatus for testing can be structured as shown in FIGS. 2 and 3. To be more specific, the illuminating apparatus for testing is composed of an illuminating means 6 having a predetermined illumination angle S; a first total reflection mirror 7 for changing the orientation of the optical axis 6A of the light emitted from the illuminating means 6 to a nearly orthogonal direction; a second total reflection mirror 8 for changing the orientation of the optical axis 6B of the light reflected by the first total reflection mirror 7 to a nearly orthogonal direction, thereby turning the reflected light to the direction opposite to the direction the illuminating means 1 emits light; a first Fresnel lens 9 as a first lens for converging the light reflected by the second total reflection mirror 8 and converting it into collimated light; a second Fresnel lens 10 that is a second lens for converging the light which has passed through through-holes 3A formed in a catalyst 3 for the automobile as the tested target after having been emitted from the first Fresnel lens 9 as the collimated light and that is the workbench of the catalyst 3; a third total reflection mirror 11 for changing the orientation of the optical axis 6C of the light emitted from the second Fresnel lens 10 to a nearly orthogonal direction; and a fourth total reflection mirror 13 for changing the orientation of the optical axis 6D of the light reflected by the third total reflection mirror 11 to a nearly orthogonal direction and for turning the reflected light to the same direction as the direction the illuminating means 6 emits light, thereby making the imaging means 12 such as a CCD camera take in the light. The two total reflection mirrors 7, 8 on the light-emitting side and the two total reflection mirrors 11, 13 on the light-receiving side are composed of the same kind and set at the same installation angle with respect to the light to be reflected. This can arrange the illuminating means 6 and the imaging means 12 on the same side and miniaturize the illuminating apparatus for testing in the horizontal direction; however, it is possible not to arrange them on the same side. If the optical axis 6A of the illuminating means 6 and the optical axis 6E to the imaging means 12, that is, the imaging center axis of the imaging means 12 are made to coincide with each other, then the illuminating apparatus for testing can be further smaller in the horizontal direction; however, the miniaturization can be achieved without making them coincide with each other. The L shown in FIG. 3 is a transparent member such as a transparent glass board, a transparent synthetic resin board, or a transparent silicone sheet, and is preferably disposed for the purpose of preventing the surface of the second Fresnel lens 10 from being damaged by the catalyst 3 mounted thereon.

After having a wider illumination angle by the two total reflection mirrors 7 and 8, the light emitted from the illuminating means 6 is converted into collimated light by the first Fresnel lens 9. The collimated light is applied to the holes 3A of the catalyst 3 mounted on the second Fresnel lens 10, and the light which has passed through the holes 3A and the light which has passed outside the catalyst 3 are converged by the second Fresnel lens 10 and further converged by the two total reflection mirrors 11 and 13, and taken into the imaging means 12. Widening the angle of the light from the illuminating means 6 at two stages by the two total reflection mirrors 7, 8 is advantageous to miniaturize the illuminating means 6; however, only one total reflection mirror could be adopted. Instead of using the total reflection mirrors 11, 13 to gather the light converged by the second Fresnel lens 10, light-converging lenses or the like can be used.

According to the invention, firstly, it becomes possible to examine a tested target with through-holes only by providing an illuminating means having a predetermined illumination angle; a first lens for converging light from the illuminating means and converting the light into collimated light; and a second lens for converging light which has passed through through-holes formed in a tested target after having been emitted from the first lens as the collimated light and for making an imaging means take in the light. It goes without saying that this apparatus can reduce cost as compared with the apparatus utilizing an illuminating means for emitting collimated light. In addition, utilizing the illuminating means for emitting light with an illumination angle can miniaturize the illuminating means itself. Furthermore, the conventional telecentric lens becomes unnecessary, thereby further reducing the cost.

According to the invention, secondarily, an illuminating apparatus for testing is composed of: an illuminating means having a predetermined illumination angle; a first total reflection mirror for changing the orientation of the optical axis of light emitted from the illuminating means to a nearly orthogonal direction; a second total reflection mirror for changing the orientation of the optical axis of light reflected by the first total reflection mirror to a nearly orthogonal direction, thereby turning the reflected light to the direction opposite to the direction the illuminating means emits light; a first lens for converging the light reflected by the second total reflection mirror and converting the light into collimated light; a second lens for converging light which has passed through through-holes formed in a tested target after having been emitted from the first lens as the collimated light; a third total reflection mirror for changing the orientation of the optical axis of light from the second lens to a nearly orthogonal direction; and a fourth total reflection mirror for changing the orientation of the optical axis of the light reflected by the third total reflection mirror to a nearly orthogonal direction, thereby making an imaging means take in the reflected light towards the same direction as the direction the illuminating means emits light. This can miniaturize not only the illuminating means but also the illuminating apparatus when the illuminating means and the imaging means are displaced from the direction to radiate the tested target, as compared with the case where they are aligned in the direction of illumination.

According to the invention, thirdly, the illuminating apparatus can be further miniaturized by adopting Fresnel lenses as the first lens and the second lens. Fresnel lenses, which are readily processed, can be made square-shaped or drilled, thereby making the apparatus advantageous in terms of manufacture.

According to the invention, fourthly, the illuminating apparatus for testing can be miniaturized in the direction orthogonal to the direction of illumination by arranging the illuminating means and the imaging means on the same side so that the optical axis of the illuminating means and the imaging center axis of the imaging means are substantially in a coaxial position. This is advantageous in terms of installation space.

According to the invention, fifthly, forming the second lens into the workbench of the tested target not only makes a special workbench unnecessary but also puts the tested target as close to the imaging means as possible, thereby making the invention advantageous in terms of cost, examination, and measurement.

What is claimed is:

1. An illuminating apparatus for testing for clogging of through-holes extending through a target to be tested, comprising: an illuminating means having a predetermined illumination angle; a first lens for converging light from said illuminating means and converting the light into collimated light for passage through the through-holes; and a second lens for converging light which has passed through the through-holes after having been emitted from the first lens as the collimated light and for making an imaging means take in the light; and wherein said illuminating means and said imaging means are arranged on the same side so that an optical axis of said illuminating means and an imaging center axis of said imaging means are substantially in a coaxial position.

2. The illuminating apparatus for testing of claim 1, wherein the first lens and the second lens are Fresnel lenses.

3. The illuminating apparatus for testing of claim 1, wherein said tested target is a catalyst for automobiles.

* * * * *